United States Patent [19]

Karakelle et al.

[11] Patent Number: 5,061,254
[45] Date of Patent: Oct. 29, 1991

[54] THERMOPLASTIC ELASTOMERIC HYDROPHILIC POLYETHERURETHANE EXPANDABLE CATHETER

[75] Inventors: Mutlu Karakelle, Dayton; Donald D. Solomon, Spring Valley, both of Ohio

[73] Assignee: Becton, Dickinson and Company, Franklin Lakes, N.J.

[21] Appl. No.: 499,154

[22] Filed: Mar. 26, 1990

Related U.S. Application Data

[63] Continuation-in-part of Ser. No. 369,484, Jun. 21, 1989, abandoned.

[51] Int. Cl.$^5$ .............................................. A61M 5/32
[52] U.S. Cl. ...................................... 604/265; 604/282
[58] Field of Search ................ 604/264, 265, 280, 282

[56] References Cited

U.S. PATENT DOCUMENTS

| | | | |
|---|---|---|---|
| 4,371,686 | 2/1983 | Yamamoto et al. | 528/76 |
| 4,424,305 | 1/1984 | Gould et al. | 525/127 |
| 4,454,309 | 6/1984 | Gould et al. | 525/454 |
| 4,647,643 | 3/1987 | Zdrahala et al. | 528/28 |
| 4,668,221 | 5/1987 | Luther | 604/164 |
| 4,678,660 | 7/1987 | McGary et al. | 424/25 |
| 4,689,386 | 8/1987 | Chapman et al. | 528/71 |
| 4,728,322 | 3/1988 | Walker et al. | 604/165 |
| 4,780,512 | 10/1988 | Gould et al. | 525/454 |
| 4,781,703 | 11/1988 | Walker et al. | 604/264 |
| 4,789,720 | 12/1988 | Teffenhart | 528/76 |
| 4,790,817 | 12/1988 | Luther | 604/53 |
| 4,798,597 | 1/1989 | Vaillancourt | 604/265 |
| 4,798,876 | 1/1989 | Gould et al. | 525/457 |
| 4,810,582 | 3/1989 | Gould et al. | 128/849 |
| 4,883,699 | 11/1989 | Aniuk et al. | 604/264 |

*Primary Examiner*—C. Fred Rosenbaum
*Assistant Examiner*—Sharon Finkel
*Attorney, Agent, or Firm*—Richard E. Brown

[57] ABSTRACT

A melt extruded catheter of thermoplastic elastomeric hydrophilic polyurethane synthesized from a diisocyanate, polyethyleneoxide glycol of high molecular weight and a chain extender expands to a larger lumen size when contacted with an aqueous liquid. The catheter may include an antithrombogenic agent, antiinfective agent and radiopaque agent. The hydrophilic polyurethane may be synthesized by one-shot bulk polymerization, and may be melt extruded into the catheter tubing, and may encapsulate a stripe of a stiffening polyurethane.

22 Claims, 3 Drawing Sheets

THERMOPLASTIC ELASTOMERIC HYDROPHILIC POLYETHERURETHANE EXPANDABLE CATHETER

This application is a continuation in-part of application Ser. No. 369,484, filed June 21, 1989, now abandoned.

BACKGROUND OF THE INVENTION

1. Field of the Invention

This invention relates to catheterization of a patient, and more particularly relates to a catheter which expands to a larger gauge size when it comes into contact with an aqueous liquid.

2. Background of the Invention

Catheterization procedures conventionally include puncture of a patient's skin and insertion of a catheter into a body cavity, such as the blood stream, using some type of catheter insertion device. For patient comfort, it is highly desirable that the catheter, and perforce any insertion equipment, be of the smallest possible cross-sectional area during insertion. It is nevertheless evident that the catheter lumen must be large enough to achieve the required rate of administration of a medicament solution through the catheter.

Catheters of the prior art have generally been made of rigid polymeric materials which do not substantially change in cross section when contacted with a body fluid. Exemplary of such conventional catheters is the Insyte ® line of catheters available from the Deseret division of Becton, Dickinson and Company, Sandy, Utah.

Recently, hydrophilic polymers which absorb water and expand, often termed hydrogels, have been disclosed. Gould et al., in U.S. Pat. No. 4,454,309 discloses hydrophilic polyurethane diacrylate thermoset compositions which swell on insertion in water and may be molded and cured to form shaped products.

U.S. Pat. No. 4,883,699 to Aniuk et al. discloses a tubing having a nonhydrophilic polyurethane component and a hydrophilic polyvinyl alcohol component. The tubing is said to absorb water and swell while retaining tensile strength.

U S. Pat. Nos. 4,728,322 and 4,781,703 to Walker et al. disclose catheters fabricated of a composition which includes a nonhydrophilic first component and a hydrophilic polyurethane diacrylate second component. When contacted with a liquid, the composition swells and softens due to absorption of the liquid, causing the catheter to increase in cross sectional area.

In similar fashion, U.S. Pat. No. 4,668,221 to Luther discloses a catheter made of hydrophilic polymer which fits over a stylet for insertion. The catheter, on contact with blood, swells and softens so that the stylet can be removed.

While the above disclosures have advanced the art of catheter design, further improvements are needed. The present invention addresses this need.

SUMMARY OF THE INVENTION

A catheter tubing comprises a thermoplastic, elastomeric, hydrophilic polyetherurethane (HPEU) or a mixture of the HPEU with a stiffening polyurethane. The HPEU has a hard segment (HS) content of 25 to 65% and is the reaction product of at least a diisocyanate, a polyglycol component containing at least 50% polyethyleneoxide glycol (PEG) and a chain extender.

In the present disclosure, all percentages are by weight. The stiffening polyurethane may have a HS content of 50 to 90% and/or a water absorption of about 10% or less. The mixture may include a uniform blend of about 50 to 99% of the HPEU and 1 to 50% of the stiffening polyurethane.

In another embodiment of the invention, a stripe of the stiffening polyurethane may be encapsulated by the HPEU.

The tubing is formed by melt processing methods such as extrusion and does not require any curing or crosslinking. When the tubing is brought into contact with an aqueous liquid, it absorbs the liquid and expands whereby the lumen increases in cross-sectional area.

The HPEU of the preferred catheter of the invention is the reaction product of high molecular weight PEG, 4,4' diphenylmethane diisocyanate (MDI) and a low molecular weight diol chain extender, and expands by absorbing 50 to 200% of its weight of water so that the lumen increases in diameter by about 5 to 50%. The most preferred HPEU is the reaction product of MDI, PEG of about 8,000 molecular weight and 1,4 butanediol (BDO) as the extender.

In other embodiments of the catheter of the invention, the HPEU may have an antithrombogenic agent such as heparin affixed to the surface, an antiinfective agent either affixed to the surface or distributed substantially evenly throughout the HPEU (hereinafter referred to as bulk distributed) or a radiopaque agent bulk distributed or associated with the HPEU in the form of one or more stripes or layers coextruded with the HPEU.

Thus, the invention provides an expandable catheter having significant advantages over prior art catheters for central venous, and particularly for vascular catheter applications. For use in peripheral intravenous applications, a smaller gauge catheter of the invention than needed for the intended medicament administration may be introduced for patient comfort and the catheter allowed to swell to the required size by contact with the patient's body fluid. In contrast to prior art expandable catheters, the catheter of the invention is made of a thermoplastic elastomeric HPEU and does not contain any catalyst, crosslinks or crosslinker by products. The HPEU or the HPEU blend of the invention is linear, melt processable, and easily formed into catheter tubing by normal heat extrusion, in contrast to the hydrogels used to fabricate most prior art expandable catheters which are not melt extrudable and require curing.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described and illustrated. The scope of the invention will be measured by the appended claims and their equivalents.

In accordance with the present invention, there is provided an expandable catheter made of an HPEU or a mixture of the HPEU and a stiffening polyurethane. When the catheter comes into contact with a body fluid, such as blood, it absorbs water and expands to a larger gauge size.

Figure 1:
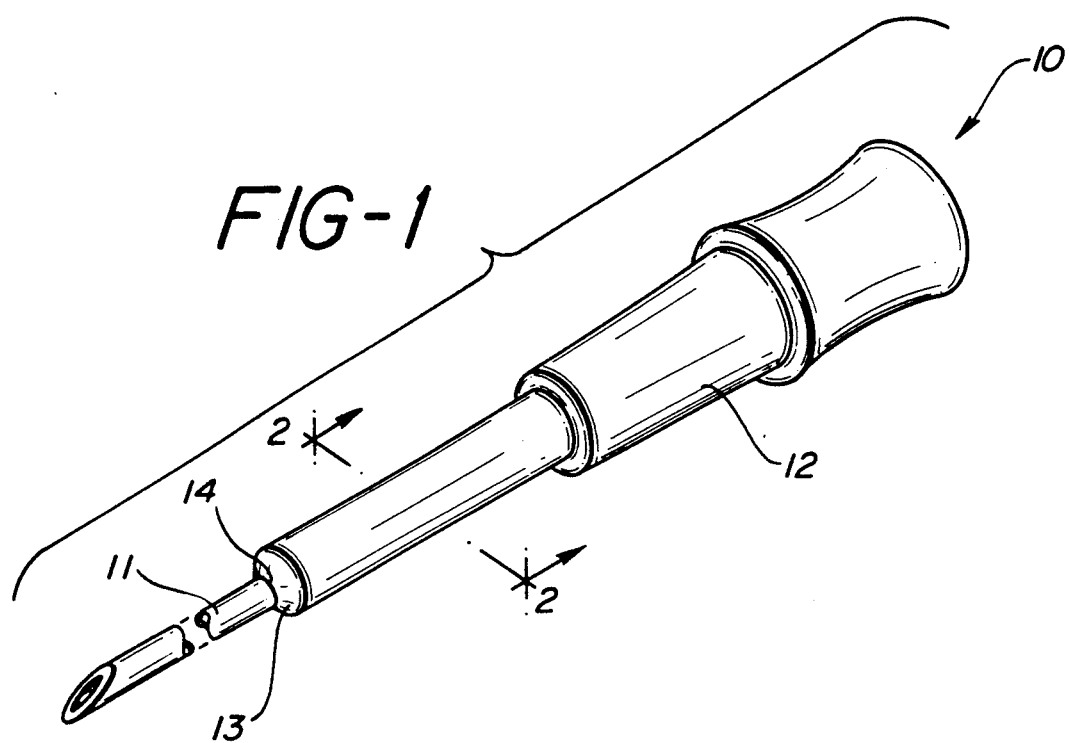
FIG. 1 is a perspective view of an intravenous catheter of the invention with associated catheter insertion device.

Adverting now to the drawings, Fig. 1 illustrates catheter tubing 10 affixed to a conventional catheter insertion device, shown as a hollow needle 11, for penetration of a patient's skin and placement of the catheter into the patient's blood stream. Catheter insertion devices are conventional in the art and do not form a part of this invention. Tubing 10 includes a body portion 12 and a gradual taper 13 leading to its point 14 of contact with needle 11.

Figure 2:
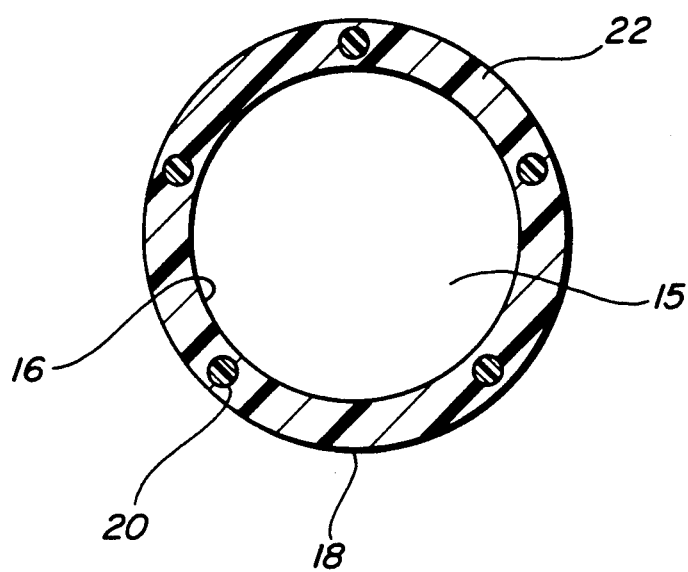
FIG. 2 is a sectional view of an embodiment of the catheter of Fig. 1 taken along the line 2-2 thereof.

A striped catheter of the invention is shown in FIG. 2 wherein tubing 10 defines a lumen 15 and has a lumen wall 16 and an outside wall 18. One or more stripes 20 of a stiffening polymer are disposed longitudinally along at least a portion of the tubing length and encapsulated in a base polymer 22. While stripe 20 is illustrated in FIG. 2 as annular in shape, it may be of any other convenient shape.

The HPEU includes three essential ingredients, a diisocyanate, PEG and a chain extender. Other components may be included as described below.

Suitable diisocyanates are aromatic diisocyanates such as MDI, 3,3'-diphenylmethanediisocyanate, alicyclic diisocyanates such as isophorone diisocyanate and 4,4'-dicyclohexylmethane diisocyanate, and aliphatic diisocyanates, as, for example, hexamethylene diisocyanate. The most preferred diisocyanate is MDI. Other diisocyanates which may be used include fluorine substituted isocyanates and silicones containing isocyanate groups.

The polyether glycol component of the HPEU may be PEG, alone or mixed with from 0 to 50% by weight of another polyglycol. Suitable polyglycols which may be mixed with the PEG include polypropyleneoxide glycol, polytetramethyleneoxide glycol (PTMEG) and a silicone glycol. Silicone glycols and PTMEG are substantially hydrophobic, and by mixing a suitable quantity of those glycols with the PEG, the degree of hydrophilicity of the HPEU blend may be tailored according to the desired extent of expansion. Silicone glycols are well-known, and representative examples are described in U.S. Pat. No. 4,647,643 to Zdrahala et al. A particularly useful silicone glycol is commercially available from Dow Corning Corp. under the designation 4-3667 fluid (formerly Q4-3667).

The PEG of the HPEU may have a molecular weight of about 650–16,000, preferably about 3,350–12,000. The most preferred PEG has a molecular weight of about 8,000. In accordance with the present invention, it has been found that the catheter made from an HPEU containing high molecular weight PEG, (PEG 8000) is stiffer when it is dry and expands significantly more upon hydration than a catheter made from an HPEU based on a low molecular weight PEG.

Suitable chain extenders may be water and/or a low molecular weight branched or unbranched diol, diamine or aminoalcohol of up to 10 carbon atoms or mixtures thereof. Representative nonlimiting examples of chain extenders are BDO; ethylene glycol; diethylene glycol; triethylene glycol; 1,2-propanediol; 1,3-propanediol; 1,6-hexanediol; 1,4-bis hydroxymethylcyclohexane, hydroquinone dihydroxyethyl ether, ethanolamine, ethylenediamine and hexamethylenediamine. Preferred chain extenders are 1,6-hexanediol, ethylenediamine, hexamethylenediamine and water, most preferably, BDO.

The percentages of the components may be such that the hard segment of the HPEU may be from about 25 to 65%, preferably from about 30 to 50% of the total weight of the formulation. From the predetermined percentage of hard segment, the proportions of the components may readily be calculated.

The HPEU of the invention has excellent wet and dry physical properties, having tensile properties in the range of 2,000–10,000 pounds per square inch (psi). It may absorb about 10–200, preferably about 50 to 150% of its weight in water wherein water absorption increases with increasing soft segment content and increasing PEG molecular weight. Upon absorption of water, a tubing extruded therefrom may increase from 5–75%, preferably about 25% in inside diameter.

The HPEU of the invention may be prepared by a one-shot or bulk synthesis method wherein all the ingredients are combined at one time. This procedure as known in the art is generally carried out with a catalyst. However, a feature of the method of the invention is that the HPEU is prepared from the components by bulk polymerization without adding a polymerization catalyst. Conventional catalysts in the art, for example, organometallic compounds such as dibutyl tin dilaurate, are leachable and may cause deleterious effects in blood contacting elements. By avoiding use of a catalyst, the HPEU of the invention is potentially purer and less toxic than those of the prior art.

Polyurethanes which may serve as the stiffening polyurethane may have a hard segment content of about 50 to 90% and/or a water absorption of about 10% or less. The isocyanate and extender components of the stiffening polyurethane may be as described above for the HPEU. The polyether glycol component may be one or more polygylcols selected to provide a water absorption of 10% or less. As is well known in the art, water absorption is enhanced by a high PEG content and reduced by a high PTMEG content. Accordingly, a preferred polyglycol for the stiffening polyurethane is PTMEG, most preferably PTMEG having a molecular weight of about 200 to 2,000. From the desired HS content and/or water absorption, the choice and ratio of polyetherglycols for the stiffening polyurethane may easily be determined. Synthesis of the stiffening polyurethane may be carried out as described above and in Example I for the HPEU.

In another embodiment of the catheter of the invention, the HPEU may be considered as a base polymer which encapsulates a longitudinal stripe of the stiffening polyurethane. The stripe prevents any substantial expansion of the catheter in the longitudinal direction which may otherwise accompany the transverse expansion due to water absorption by the HPEU.

The HPEU, alone or blended with the stiffening polyurethane may be melt extruded into tubing of any suitable size for use as catheter tubing. Likewise, the catheter of the invention having an encapsulated stripe of the stiffening polymer may also be made by extrusion or coextrusion procedures. Formation of striped or blended catheters by extrusion is well-known in the art and no further details are needed for a complete understanding of this aspect of the invention. The catheter tubing may have a range of gauge sizes from 28 gauge to 14 gauge French.

The catheter of the invention may have an antiinfective agent, a radiopaque agent or an antithrombogenic agent associated with the HPEU. Suitable antithrombogenic agents are prostaglandins, urokinase, streptokinase, tissue plasminogen activator and heparinoids. Preferred antithrombogenic agents are sulfonated heparinoids, such as dextran sulfonate, most preferably heparin. The antithrombogenic agent may be about 1 to 10, preferably about 5% by weight of the HPEU.

The antithrombogenic agent may be coated onto the surface of the expandable catheter by conventional methods. For example, a complex of heparin with a quaternary salt may be used. Such complexes are well known in the art and are described by McGary et al. in U.S. Pat. No. 4,678,660. Suitable complexes may be formed with cetylpyridinium chloride or benzalkonium chloride. Preferred complexes are those in which the heparin is complexed with dodecylmethyl ammonium chloride or, most preferably, with tridodecylmethyl ammonium chloride (conventionally referred to as TDMAC). Coating may be accomplished by dipping the tubing into a solution containing about 0.5 to 20, preferably about 2 to 8% by weight of the heparin complex and optionally about 1 to 10, preferably about 5% by weight of the HPEU in a suitable solvent or solvent combination. Exemplary of useful solvents are dimethylacetamide (DMAC), dimethylformamide, N methylpyrrolidone, toluene, methyl ethyl ketone, petroleum ether, isopropanol and propylene glycol methyl ether acetate (PGMEA). A preferred solvent is a 1:1 by volume mixture of DMAC and PGMEA.

Any conventional radiopaque agent as known in the art may be included in the HPEU of the invention, as for example, an inorganic radiopaque such as barium sulfate, bismuth trioxide or tungsten powder, an iodinated organic radiopaque, or an iodinated or brominated polyurethane. The radiopaque agent may be about 2 to 35% by weight of the catheter. The radiopaque agent may be included in the expandable catheter of the invention as one or more stripes or layers formed by conventional extrusion or coextrusion techniques.

Antiinfective agents as known in the art which may be used include chlorhexidine, silver sulfadiazine, or antibiotics such as penicillin. These materials may be surface coated onto the expandable catheter by dipping the catheter into a solution containing about 1 to 10% by weight of the anti infective agent, optionally containing about 1 to 10, preferably about 5% by weight of the HPEU. Suitable solvents are as described above. A preferred method for fabrication of the catheter is by melt extrusion. The antiinfective agent, if it is stable to the extrusion temperature, and HPEU may be blended in particulate form by any suitable mixing technique, such as stirring or tumbling the polymer pellets and antiinfective agent together, or preferably by conventional twin screw extruding. In the latter process, the ingredients may be simultaneously uniformly blended, melted and extruded into catheter tubing using a commercial twin screw extruder such as the Werner and Pfleiderer Model ZDSK 28 unit.

The expandable catheter of the invention is of constant diameter until it comes into contact with an aqueous liquid. In use, a catheter of smaller gauge size may be introduced into a patient's blood stream whereupon it absorbs water, expands, and any insertion equipment may easily be removed because of the increased size of the lumen. The larger lumen provides enhanced flow of a solution being administered to the patient.

Figure 3:
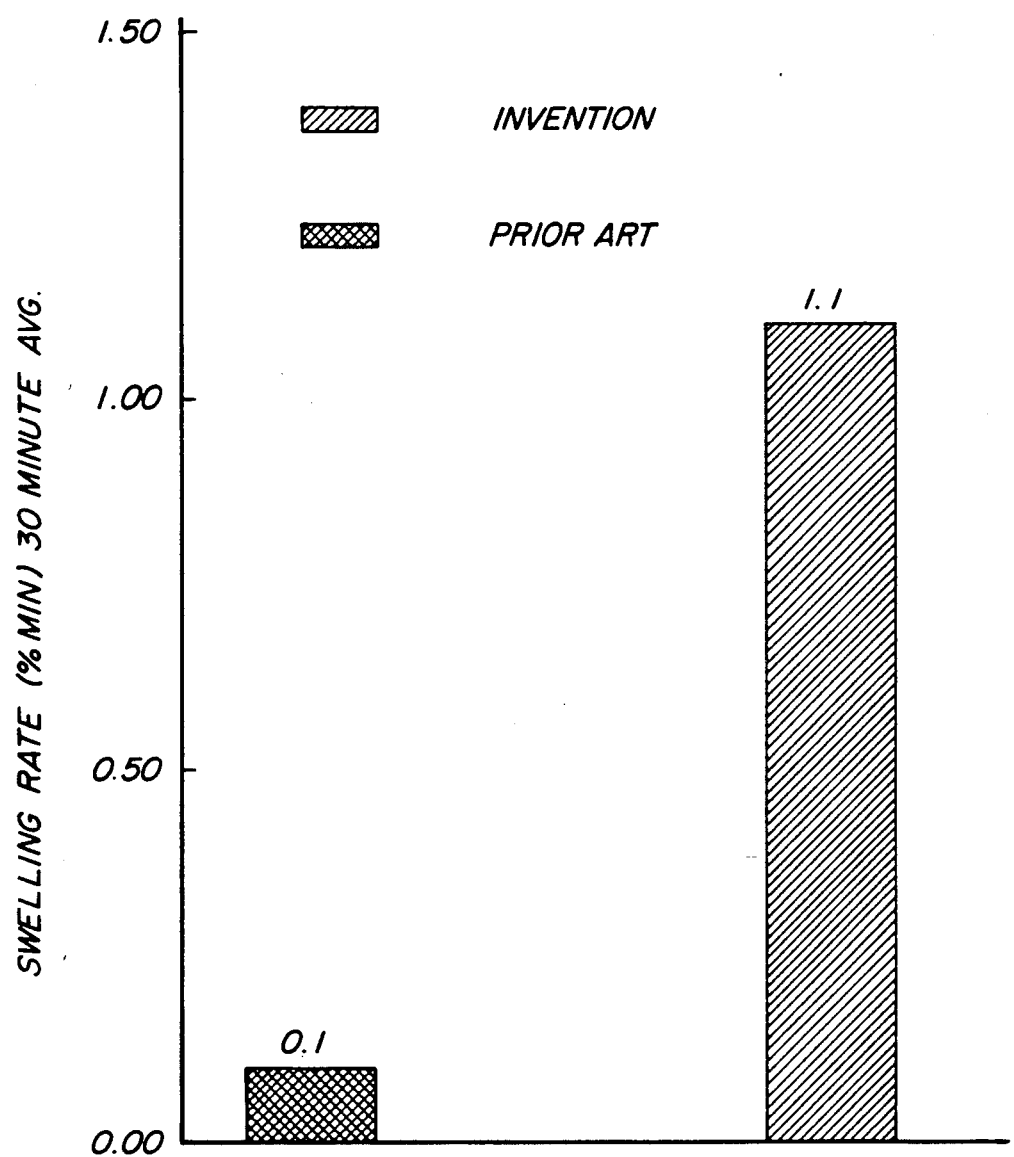
FIG. 3 illustrates the swelling rate of the catheter of the invention compared to the swelling rate of a prior art catheter.
Figure 4:
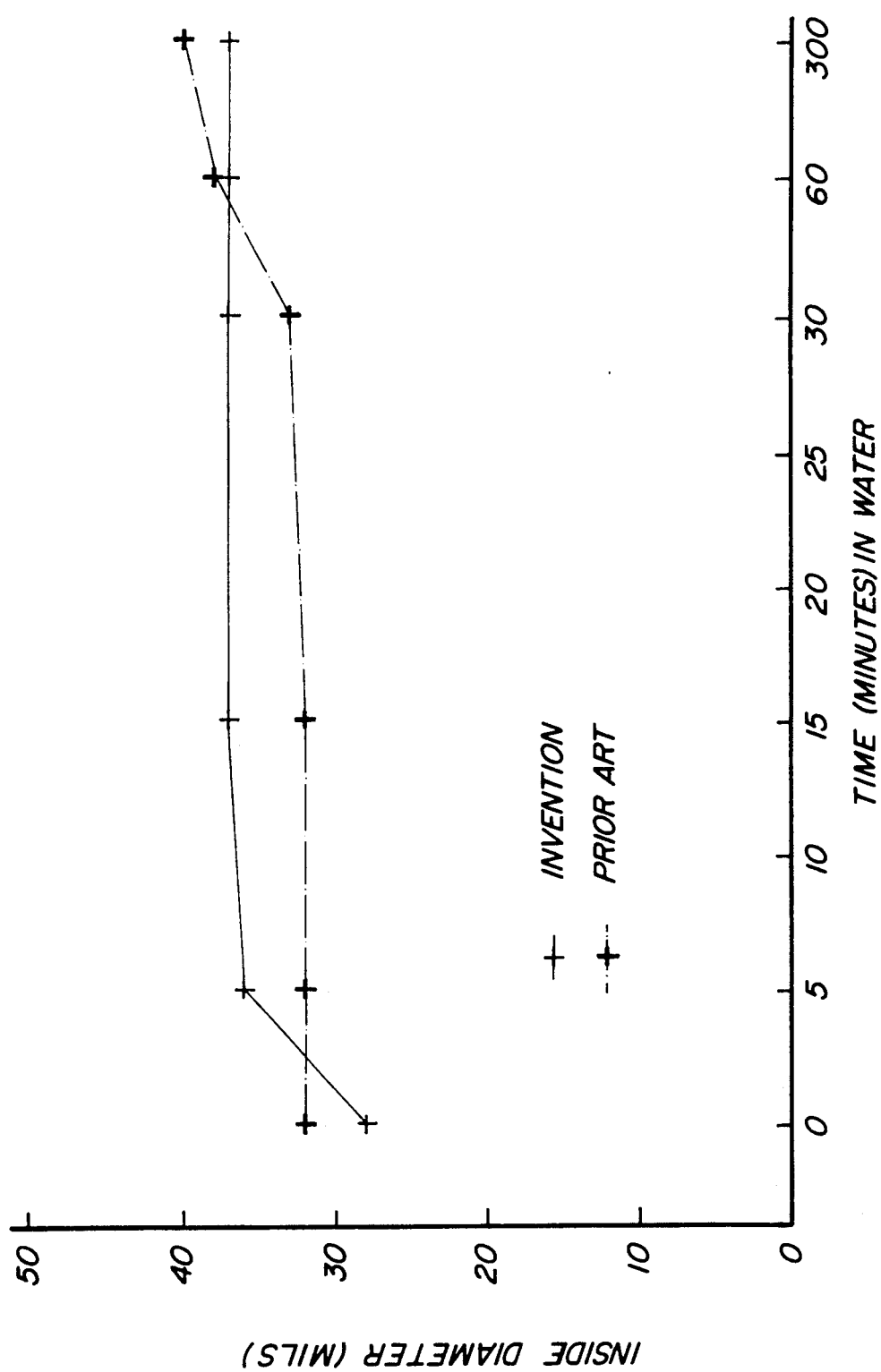
Fig. 4 compares the change in the inside diameter of the catheter of the invention and a prior art catheter as a function of time.

Comparison of the expandability of the catheter of the invention and the prior art catheter of U.S. Pat. No. 4,781,703 is illustrated in the Figures. FIG. 3 shows that, where brought into contact with water, a 20 gauge catheter of the invention having a 45% hard segment increases in inside diameter at a rate of 1.1% per minute whereas a 20 gauge, 45% hard segment expandable catheter of the prior art increases at a rate of only 0.1% per minute. FIG. 4 shows that the catheter of the invention is substantially fully expanded after only five minutes whereas expansion of the prior art catheter proceeds slowly over 30 minutes and is not complete until about 60 minutes after contact with water. It is immediately evident that this rapid rate of expansion will render the catheter of this invention highly advantageous in a hospital setting. For example, a nurse monitoring a patient's intravenous medication will know that, after only five minutes, the catheter has fully expanded and the rate of administration will thereafter remain constant. With the prior art catheter, however, the rate of administration will change over 60 or more minutes, requiring constant vigilance during this time to prevent the rate of administration from exceeding the desired rate.

The following Examples are provided to further describe the invention but are not to be considered as limitative of the invention.

EXAMPLE I

Polyurethane Synthesis

Materials

Polyglycols of various molecular weights were obtained from Union Carbide Corp. and used as received. Determination of the hydroxyl number by the phthalic anhydride-pyridine method and the water content by Karl Fisher titration were performed to verify and adjust formulation stoichiometry. 1,4-Butanediol (BDO) was used as chain extender, as received, from DuPont. MDI was received from Mobay and filtered before use.

Synthesis

Polyurethanes were synthesized using a one-shot bulk polymerization. Stoichiometric amounts of polyglycol and BDO were placed in the polymerization vessel and degassed at 60° C. for 30 minutes. Then, the stoichiometric amount of MDI (1.02 Index) was added and stirred vigorously until the polymerization temperature reached about 85° C. The polymer was discharged and postcured at 125° C. for 30 minutes. Representative HPEU formulations of the invention are given in Table I.

TABLE I

| | HPEU FORMULATIONS | | | | |
|---|---|---|---|---|---|
| No. | PEG MW | HS % | MDI % | BDO % | PEG % |
| 1 | 600 | 35 | 33.1 | 1.9 | 65 |
| 2 | 600 | 45 | 39.4 | 5.6 | 55 |
| 3 | 600 | 55 | 45.6 | 9.4 | 45 |
| 4 | 600 | 65 | 51.9 | 13.1 | 35 |
| 5 | 1450 | 35 | 28.9 | 6.1 | 65 |
| 6 | 1450 | 45 | 35.8 | 9.2 | 55 |
| 7 | 1450 | 55 | 42.8 | 12.2 | 45 |
| 8 | 1450 | 65 | 49.7 | 15.3 | 35 |
| 9 | 3350 | 35 | 27.2 | 7.8 | 65 |
| 10 | 3350 | 45 | 34.4 | 10.6 | 55 |

TABLE I-continued

HPEU FORMULATIONS

| No. | PEG MW | HS % | MDI % | BDO % | PEG % |
|-----|--------|------|-------|-------|-------|
| 11 | 3350 | 55 | 41.6 | 13.4 | 45 |
| 12 | 3350 | 65 | 48.7 | 16.3 | 35 |
| 13 | 8000 | 35 | 26.3 | 8.7 | 65 |
| 14 | 8000 | 45 | 33.6 | 11.4 | 55 |
| 15 | 8000 | 55 | 41.0 | 14.0 | 45 |
| 16 | 8000 | 65 | 48.3 | 16.7 | 35 |

EXAMPLE II

Extrusion of HPEU

HPEU slabs from Example I were chipped and extruded into medical tubing and 8 to 12 mil thick ribbons using a conventional ¾ inch or 1 inch single screw extruder. The extrusion temperature profile range was: Feeding Zone, 150° to 175° C.; Melting Zone, 190° to 220° C.; Metering Zone, 190° to 220° C. and Die, 190° to 220° C. depending on the hard segment content.

EXAMPLE III

Coextrusion of Striped Catheter

A melt stream of an HPEU from a main extruder and a melt stream of a stiffening polymer from a coextruder are maintained separately until combined in the forward, down stream portion of an extruder head. The combined streams are passed through and emerge from a tube die (coaxial or cross head) as an integral tubing member having stripes of the stiffening polymer in a continuous HPEU phase.

EXAMPLE IV

Properties of HPEU

Tensile Properties

Tensile property tests of dry (23° C. and 50% relative humidity) and hydrated (in 0.9% saline solution at 23° C.) HPEU samples were performed on die cut samples from extruded ribbons according to standard ASTM procedures and are given in Table II. The dry thickness of the test samples was used in calculation of the hydrated tensile parameters, therefore, the hydrated tensile values are not absolute and are for comparative purposes only.

TABLE II

| HPEU* | 35% HS | | 45% HS | | 55% HS | | 65% HS | |
|-------|--------|--------|--------|--------|--------|--------|--------|--------|
|       | dry | hyd** | dry | hyd** | dry | hyd** | dry | hyd** |
| tensile (psi) | 890 | 750 | 2020 | 1230 | 3090 | 2740 | 2890 | 2910 |
| 25% modulus (psi) | 530 | 250 | 1080 | 510 | 810 | 890 | 1000 | 1100 |
| 100% modulus (psi) | 590 | 520 | 1190 | 880 | 1070 | 1430 | 1350 | 1660 |
| Elongation (%) | 500 | 200 | 490 | 180 | 530 | 360 | 360 | 350 |
| T.S. Die-C (pli)*** | 290 | 60 | 490 | 160 | 220 | 220 | 300 | 270 |

*MDI, PEG-8000, BDO
**hydrated
***Tear Strength in pounds/linear inch

Water Absorption and Degree of Swelling

The water absorption and the degree of swelling were determined using 0.5 inch ×1 inch injection molded samples. These samples were kept in distilled water at room temperature (23° C.) for 24 hours, for establishing equilibrium water absorption. The samples were removed and the surface water was carefully blotted with filter paper without applying pressure. Each swollen sample was carefully weighed, vacuum dried at approximately 60° C. for 48 hours and then reweighed. The water absorption and the degree of swelling were calculated from weight difference data using the following equations:

$$WA = (Ws - Wp) / Wp \times 100 \qquad [1]$$

$$DS = [(Wp/dp) + (Ws - Wp) / dw] / (Wp/dp) \qquad [2]$$

where WA is percent water absorption, Ws is weight or swollen sample, Wp is weight of dry sample, DS is degree of swelling, dp is the density of dry sample (1.15 g/cm$^3$) and dw is the density of water (1.0 g/cm$^3$). An average polyurethane density of 1.15 g/cm$^3$ was used for all HPEU formulations.

Inside diameter was measured on samples removed from the distilled water bath at selected times.

Thus, the invention provides a catheter which, on contact with a patient's blood, expands to a larger lumen size to allow greater flow rate and concurrently stiffens to allow adjustment of the catheter position without kinking.

We claim:

1. A melt extruded catheter comprising a substantially hydrophilic thermoplastic elastomeric polyurethane tubing, said polyurethane having a hard segment of 25 to 60% and comprising the product from reaction of a mixture of a diisocyanate, a chain extender and a polyglycol component comprising from 80 to 100% of polyethyleneoxide glycol wherein the ratio of said diisocyanate to said combined polyglycol and extender components is about 1.02:1, said tubing, when brought into contact with an aqueous liquid, absorbing about 10 to 200% of its weight of said liquid and expanding whereby its inside diameter increases about 5 to 75%.

2. The catheter of claim 1 wherein said diisocyanate is selected from the group consisting of 4,4'-diphenylmethane diisocyanate, 3,3'-diphenylmethane diisocyanate, isophorone diisocyanate and hexamethylene diisocyanate.

3. The catheter of claim 1 wherein said chain extender is selected from the group consisting of 1-4-butanediol, ethylene glycol, diethylene glycol, triethylene glycol, 1,2-propanediol, 1,3-propanediol, 1,6-hexanediol, 1,4-bis hydroxymethyl cyclohexane, hydroquinone dihydroxyethyl ether, ethanolamine, ethylenediamine and hexamethylenediamine.

4. The catheter of claim 1 wherein said polyethyleneoxide glycol has a molecular weight of about 650 to 16,000.

5. The catheter of claim 1 wherein said thermoplastic elastomeric hydrophilic polyurethane further comprises a polyglycol selected from the group consisting of polypropyleneoxide glycol, polytetramethyleneoxide glycol and a silicone glycol.

6. The catheter of claim 1 further comprising an agent selected from the group consisting of an antiinfective agent, a radiopaque agent and an antithrombogenic agent.

7. The catheter of claim 6 wherein said antithrombogenic agent is selected from the group consisting of a prostaglandin, urokinase, streptokinase, tissue plasminogen activator and a heparinoid.

8. The catheter of claim 6 wherein said antiinfective agent is selected from the group consisting of chlorhexidine, silver sulfadiazine and an antibiotic.

9. The catheter of claim 6 wherein said radiopaque agent is selected from the group consisting of an inorganic radiopaque and an iodinated organic radiopaque.

10. A melt extruded catheter comprising a substantially hydrophilic thermoplastic elastomeric polyurethane tubing, said polyurethane having a hard segment of about 30 to 45% and comprising the product from reaction of 4,4'-diphenylmethane diisocyanate, 1,4-butanediol and polyglycol fraction consisting essentially of polyethyleneoxide glycol of molecular weight from about 600 to about 8,000 wherein the ratio of said diisocyanate to said combined polyglycol and 1,4-butanediol is about 1.02:1, said tubing, when brought into contact with an aqueous liquid, absorbing about 50 to 100% of its weight of said liquid and expanding whereby its inside diameter increases about 25%.

11. A melt extruded catheter comprising a substantially hydrophilic thermoplastic elastomeric base polyurethane tubing encapsulating a stripe of a stiffening polyurethane, said base polyurethane having a hard segment of 25% to 65% and comprising the product from reaction of a mixture of a first diisocyanate, a first chain extender and a first polyglycol component, said second polyglycol component comprising at least 50% of polyethyleneoxide glycol, said stiffening polyurethane comprising the reaction product of a second diisocyanate, a second chain extender and a second polyglycol component, said second polyglycol component consisting essentially of polytetramethyleneoxide glycol, said stiffening polyurethane having a hard segment content of 50 to 90% and a water absorption of no more than 10%.

12. The catheter of claim 11 wherein said first and second diisocyanates are selected from the group consisting of 4,4'-diphenylmethane diisocyanate, 3,3'-diphenylmethane diisocyanate, isophorone diisocyanate and hexamethylene diisocyanate.

13. The catheter of claim 11 wherein said first and second chain extenders are selected from the group consisting of 1-4-butanediol, ethylene glycol, diethylene glycol, triethylene glycol, 1,2-propanediol, 1,3-propanediol, 1,6-hexanediol, 1,4-bis-hydroxymethyl cyclohexane, hydroquinone dihydroxyethyl ether, ethanolamine, ethylenediamine and 14. The catheter of claim 11 wherein said polyethyleneoxide glycol has a molecular weight of about 650 to 16,000.

15. The catheter of claim 11 wherein said base polyurethane further comprises a polyglycol selected from the group consisting of polypropyleneoxide glycol, polytetramethyleneoxide glycol and a silicone glycol.

16. The catheter of claim 11 wherein said base polyurethane further comprises an agent selected from the group consisting of an antiinfective agent, a radiopaque agent and an antithrombogenic agent.

17. The catheter of claim 16 wherein said antithrombogenic agent is selected from the group consisting of a prostaglandin, urokinase, streptokinase, tissue plasminogen activator and a heparinoid.

18. The catheter of claim 16 wherein said antiinfective agent is selected from the group consisting of chlorhexidine, silver sulfadiazine and an antibiotic.

19. The catheter of claim 16 wherein said radiopaque agent is selected from the group consisting of an inorganic radiopaque and an iodinated organic radiopaque.

20. A melt extruded catheter comprising a substantially hydrophilic thermoplastic elastomeric base polyurethane tubing encapsulating a stripe of a stiffening polyurethane, said base polyurethane having a hard segment of 30 to 45% and comprising the product from reaction of a mixture of 4,4'-diphenylmethane diisocyanate, 1-4-butanediol, and a polyglycol component comprising at least 50% of polyethyleneoxide glycol having a molecular weight of 6,000 to 12,000, said stiffening polyurethane comprising the reaction product of 4,4'-diphenylmethane diisocyanate, 1,4-butanediol and polytetramethyleneoxide glycol said tubing when brought into contact with an aqueous liquid absorbing about 50 to 150% of its weight of said liquid and expanding whereby its inside diameter increases about 5 to 50%.

21. The catheter of claim 20 wherein said stiffening polymer has a hard segment content of 50 to 90%.

22. The catheter of claim 20 wherein said stiffening polymer has a water absorption of no more than 10%.

* * * * *